united States Patent [19]

Hitzman

[11] 4,169,762

[45] Oct. 2, 1979

[54] SELF-TOXIFICATION PROCESS FOR AEROBIC FERMENTATION

[75] Inventor: Donald O. Hitzman, Bartlesville, Okla.

[73] Assignee: Phillips Petroleum Company, Bartlesville, Okla.

[21] Appl. No.: 827,761

[22] Filed: Aug. 25, 1977

[51] Int. Cl.² .......................... C12B 1/08; C12B 1/20
[52] U.S. Cl. ..................................... 435/243; 435/813
[58] Field of Search ............... 195/28 R, 49, 108, 109, 195/110, 115, 117, 121

[56] References Cited

U.S. PATENT DOCUMENTS

| | | | |
|---|---|---|---|
| 3,616,224 | 10/1971 | Shilo et al. ............................. | 195/49 |
| 3,764,476 | 10/1973 | Abe et al. ............................... | 195/49 |
| 3,834,989 | 9/1975 | Harrison .............................. | 195/28 R |

OTHER PUBLICATIONS

Anthony et al., "The Microbial Oxidation of Methanol", *Biochem. J.*, vol. 92, pp. 609–614 (1964).

Ogata et al., "A Yeast Capable of Utilizing Methanol", *Agr. Biol. Chem.*, vol. 33, No. 10, pp. 1519–1520 (1969).
Levine et al., "Isolation and Characterization of a Thermotolerant Methanol–Utilizing Yeast", *Applied Microbiology*, vol. 26, No. 6, pp. 982–990 (1973).
Cook, *The Chemistry and Biology of Yeasts*, Academic Press, Inc., New York, (1958), pp. 256–275.

*Primary Examiner*—Thomas G. Wiseman

[57] ABSTRACT

During the aerobic fermentation process, when it is desired to kill the microorganism, a growth essential material such as the carbon source or the oxygen source is interrupted for a period of time sufficient to lower the concentration of the material to a level at which the microorganism substantially ceases to propagate. After this concentration has been reached, flow of the material is then rapidly reestablished in a quantity so that the concentration of the material in the fermentation medium is such that the microorganism will generate a toxic amount of formaldehyde and thereby kill the microorganism.

19 Claims, No Drawings

SELF-TOXIFICATION PROCESS FOR AEROBIC FERMENTATION

The present invention relates to a process for the propagation of microbial cells and more particularly to the termination of the propagation of these cells by toxifying the fermentation medium. It is known in the art how to produce single cell protein (SCP) by the aerobic fermentation of a microorganism on a suitable carbonaceous material as a carbon source which is assimilable by the propagating microorganism. Current world-wide food shortages and impending food shortages have encouraged the research and development of methods for producing high quality, low cost microbial protein, i.e., SCP to alleviate these food shortages. Many methods are known for producing protein by fermentation methods.

The present invention can be regarded as a method for terminating the propagation of the microorganisms, that is, stopping the multiplication, propagation or growth of the microbial cells, during or after the fermentation process. As commonly practiced in the art, heating, such as by the application of steam in contact with the microbial cells, has been used with some success to terminate the propagation thereof, that is, to kill the cells so that same can be used for its intended end use. However, heating microbial cells poses some problems in that some of the nutritional values of the cells can be decreased significantly by the application of excessive heat. Also, heating requires the expenditure of substantial energy which would not otherwise be required. Further, it has been found that certain biocidal agents can be added to the fermentation medium in a concentration sufficient to prevent or terminate the propagation. However, such biocidal agents also pose problems in that the biocidal agent may be toxic to an end user of the microbial cells. This would then require the removal of the biocidal agent from the microbial cells before the cells can be used. The use of additive biocidal agents for termination is an expensive process.

It has been found that formaldehyde is both a biocidal agent to certain microorganisms and an intermediate metabolite which, in sufficiently low quantities, can be assimilated by the microorganism as a food or carbon source. However, if the concentration of the formaldehyde is sufficiently high, the formaldehyde will act as a biocidal agent and terminate the life of the microbial cells. It is known in the art that formaldehyde can be added to a fermentation medium to prevent or terminate the propagation of the cells. It is also known that formaldehyde can be added to new fermentation medium before same is introduced into the fermentation vessel to maintain the new medium in a sterile condition and upon entering the vessel the formaldehyde is diluted sufficiently by the existing medium so as to not be toxic to the microbial cells.

The present invention provides a process for developing in situ a sufficient quantity of formaldehyde so that it will be toxic to the microbial cells for the substantial termination of the propagation thereof. The present invention can be practiced in either batch or continuous type fermentation processes and is particularly well adapted for foam-type processes such as that disclosed in U.S. Pat. No. 3,982,998, issued Sept. 28, 1976.

The principal objects and advantages of the present invention are: to provide a process for developing in situ a biocidal agent in a concentration sufficient to toxify the process and substantially terminate propagation of microbial cells; to provide such a process which is efficient and requires a minimum of down time for fermentation equipment; to provide such a process which is adaptable for numerous microorganisms; and to provide such a method which is well adapted for its intended use.

Other objects and advantages of the present invention will become apparent from the following detailed description wherein are set forth by way of illustration and example certain embodiments of the present invention.

Generally, the present invention provides a method whereby in an aerobic fermentation process of either a batch or continuous type the fermentation operating conditions are deliberately upset of changed in order to cause the microorganism to generate a toxic amount of a biocidal agent, such as an aldehyde, from the metabolism of the carbon source thus causing self toxification, or death, of the microorganism (also referred to as microbial cells) by the generated biocidal agent. Hereinafter the biocidal agent will be referred to as, but not limited to, formaldehyde which is a preferred biocidal agent. The fermentation process can also be of a foam or non-foam type process wherein a carbon source assimilable by the microorganism, a source of oxygen, a source of assimilable nitrogen and other trace elements and minerals are in admixture and contain a microorganism capable of propagating, i.e., multiplying or growing, to produce an end product such as single cell protein. The abovecited patent discloses such a process with the disclosure therein being incorporated by reference. Certain levels of the various and assorted materials used in the fermentation process are maintained, as is known in the art, so as to efficiently produce single cell protein or the like. Normally such processes are exothermic and require the removal of heat therefrom.

It has been found that by upsetting the conditions of the fermentation process, in a manner described below, a toxic amount of formaldehyde is formed and is toxic to the microorganism and thereby render same non-viable. The present invention includes within its scope fermentation processes which according to the type of microorganism used and its carbon source can produce a toxic metabolite during the metabolism of a material present in the fermentation medium. If the microorganism is either unable to metabolize the toxic metabolite fast enough to prevent its toxic effect, or is unable to survive the levels of the toxic metabolite generated initially then the toxic metabolite is not further utilized in the metabolic assimilation chain by the microorganism. This is accomplished by starving the microorganism of one or more of the growth essential materials as, for example, the carbon source or the oxygen source for a time sufficient to lower the concentration of that material substantially to a level at which the microorganisms will substantially cease to propagate or multiply but yet not be rendered non-viable. After this reduced concentration condition has been obtained, the material which was starved from the microorganisms is introduced into the fermentation medium in a quantity sufficient for the microorganism to generate a toxic concentration of aldehyde and thereby kill the microorganism or render same non-viable.

The present invention particularly deals with the type of process in which the microorganism is unable to metabolize the toxic metabolite fast enough to prevent its toxic effect. More particularly, the present invention relates to such processes which produce an aldehyde as a toxic metabolite during the fermentation process. Aldehydes are well known for their toxic effect on microorganisms, especially the lower aldehydes of 1 to about 6 carbon atoms per molecule and more especially formaldehyde. It is known that microorganisms capable of utilizing alkanes, e.g., methane or n-hexane, and/or primary alcohols, e.g., methanol or ethanol, as the carbon/energy source can utilize the corresponding aldehyde, e.g., formaldehyde or acetaldehyde, in the metabolic assimilation chain. The produced aldehydes are toxic metabolites in aerobic microbial processes in which the carbon/energy source charged to the fermentation system is an alkane or primary alcohol.

In order to achieve the rendering of a microorganism non-viable by means of an in situ produced toxic metabolite, it is currently believed necessary to deprive the microorganism for a brief period of time of at least one growth essential material. Such growth essential materials include preferably oxygen or the carbon/energy source. The brief period of starvation is believed to cause the enzyme system of the microorganism to deadapt with regard to its ability to metalolize the toxic metabolite sufficiently rapidly to prevent the toxic effect of the toxic metabolite from being exhibited. Thus, following the enzyme deadaptation, the reintroduction of the growth essential material of which the microorganism was starved causes renewed production of the toxic metabolite. Now, the enzyme system of the microbe is unable to assimilate the toxic metabolite, at least with sufficient rapidity whereby the toxic metabolite quickly builds to a toxic level which causes the death of the microorganism.

It is believed that the sudden introduction of a high concentration of a growth essential material will not achieve the rendering of the microorganisms non-viable. This is believed due to the fact that without the starvation, there is no deadaptation of the enzyme system thereby preventing the buildup of a toxic metabolite.

The present invention is preferably carried out in a vessel or holding tank other than the fermenter. The fermentation medium desired to be treated is transferred from the fermenter to the vessel or holding tank prior to the cell separation step. However, it is to be noted that the present invention can also be carried out in the fermenter if desired.

In the following description, reference will be made particularly to methanol as the carbon source, which is a preferred embodiment of this invention, however, it is to be understood that other carbon sources can also be used. A preferred group of carbon sources are the alcohols having from 1 to 16 carbon atoms and mixtures of any two or more thereof. Any microorganism which when same consumes the carbon source produces a toxic metabolite such as an aldehyde, can be used in the present invention. Suitable microorganisms can be selected from bacteria, yeasts and fungi and mixtures of any two or more.

Suitable yeasts include species or mixtures of species from the genera Candida, Hansenula, Torulopsis, Saccharomyces, Pichia, Debaryomyces, Lipomyces, Cryptococcus, Nematospora, Brettanomyces and Trichosporon. The preferred genera include Candida, Hansenula, Torulopsis, Pichia, and Saccharomyces. Examples of suitable species include:

*Candida boidinii*
*Candida mycoderma*
*Candida utilis*
*Candida stellatoidea*
*Candida robusta*
*Candida claussenii*
*Candida rugosa*
*Candida subtropicalis*
*Candida petrafilium*
*Candida novellus*
*Candida tropicalis*
*Candida lipolytica*

*Brettanomyces petrophilium*

*Hansenula minuta*
*Hansenula saturnus*
*Hansenula californica*
*Hansenula mrakii*
*Hansenula silvicola*
*Hansenula polymorpha*
*Hansenula wickerhamii*
*Hansenula capsulata*
*Hansenula glucozyma*
*Hansenula henricii*
*Hansenula nonfermentans*
*Hansenula philodendra*
*Hansenula alcolica*

*Torulopsis candida*
*Torulopsis bolmii*
*Torulopsis versatilis*
*Torulopsis glabrata*
*Torulopsis molishiana*
*Torulopsis nemodendra*
*Torulopsis nitratophila*
*Torulopsis pinus*
*Torulopsis xylinus*
*Torulopsis methanosorba*
*Torulopsis petrofilium*
*Torulopsis utilis*

*Pichia farinosa*
*Pichia polymorpha*
*Pichia membranefaciens*
*Pichia pinus*
*Pichia pastoris*
*Pichia trehalophila*
*Pichia guilliermondii*
*Pichia methanolophilia*
*Pichia methanolica*

*Saccharomyces cerevisiae*
*Saccharomyces fragilis*
*Saccharomyces rosei*
*Saccharomyces acidifaciens*
*Saccharomyces elegans*
*Saccharomyces methanonforms*

*Trichosporon alcophilum*
*Trichosporon butanophilum*

*Saccharomyces rouxii*
*Saccharomyces lactis*
*Saccharomyces fractum*

Suitable bacteria include species or mixtures of species from the genera Bacillus, Aeromonas, Mycobacterium, Actinomyces, Nocardia, Pseudomonas, Methanomonas, Protaminobacter, Methylococcus, Arthrobacter, Methylomonas, Brevibacterium, Acetobacter, Micrococcus, Rhodopseudomonas, Corynebacterium, Cellumonas, Microbacterium, Achromobacter, Methylobacter, Methylosinus and Methylocystis. Preferred genera include Bacillus, Pseudomonas, Protaminobacter, Micrococcus, Arthrobacter and Corynebacterium.

Examples of suitable species include:

Bacillus subtilus
Bacillus cereus
Bacillus aureus
Bacillus acidi
Bacillus urici
Bacillus coagulans
Bacillus mycoides
Bacillus circulans
Bacillus megaterium
Bacillus licheniformis Pseudomonas methanolica
Pseudomonas ligustri
Pseudomonas orvilla
Pseudomonas methanica
Pseudomonas fluorescens
Pseudomonas aeruginosa
Pseudomonas oleovorans
Pseudomonas putida
Pseudomonas borepolis
Pseudomonas pyocyanea
Pseudomonas methylphilus
Pseudomonas brevis
Pseudomonas acidovorans
Pseudomonas methanoloxidans
Pseudomonas aerogenes
Pseudomonas extorquens
Pseudomonas utilis
Pseudomonas japonica
Pseudomonas insuata
Pseudomonas methylonica Protaminobacter ruber
Protaminobacter candidus
Protaminobacter microcyclus
Protaminobacter serratia
Protaminobacter thiaminophagus Corynebacterium simplex
Corynebacterium hydrocarbooxydans
Corynebacterium alkanum
Corynebacterium oleophilus
Corynebacterium hydrocarboclastus
Corynebacterium glutamicum
Corynebacterium viscosus
Corynebacterium dioxydans
Corynebacterium methanophilum
Corynebacterium paraldehydium
Corynebacterium acetoacedophilum Micrococcus cerificans
Micrococcus rhodius Aeromonas methanolphilum Cellumonas galba Arthrobacter rufescens
Arthrobacter parafficum Arthrobacter simplex
Arthrobacter citreus
Arthrobacter alkanicus Methanomonas methanica
Methanomonas methanooxidans Methylomonas agile
Methylomonas albus
Methylomonas rubrum
Methylomonas methanolica Mycobacterium rhodochrous
Mycobacterium phlei
Mycobacterium brevicale Nocardia salmonicolor
Nocardia minimus
Nocardia corallina
Nocardia butanica Rhodopseudomonas capsulatus Microbacterium ammoniaphilum
Microbacterium flavum Archromobacter butanicum
Archromobacter coagulans
Archromobacter methanoloxidans Brevibacterium butanicum
Brevibacterium roseum
Brevibacterium flavum
Brevibacterium lactofermentum
Brevibacterium paraffinolyticum
Brevibacterium ketoglutamicum
Brevibacterium insectiphilium Methylococcus capsulatus Suitable fungi include species or mixtures of species from the genera Aspergillus, Monilia, Rhizopus, Penicillium, Mucor, Alternaria, Helminthosporium, Gillerella and Fusarium.

Examples of suitable species of fungi include:

Aspergillus niger
Aspergillus glaucus
Aspergillus flavus
Aspergillus terreus
Aspergillus itconicus Penicillium notatum
Penicillium chrysogenum
Penicillium glaucum
Penicillium griseofulvum
Penicillium expansum
Penicillium digitatum
Penicillium italicum Rhizopus nigricans
Rhizopus oryzae
Rhizophus delemar
Rhizopus arrhizus
Rhizopus stolonifer Gibberella fujikurio

*Fusarium moniliforme*

*Mucor mucedo*
*Mucor genevensis*

The above list is not to be construed as complete or exclusive.

Two embodiments are disclosed below and are not to be construed as being exclusive of variations of the present invention.

In one embodiment the self toxification is achieved by the interruption of the carbon source feed to the fermentation zone. The carbon source feed, such as methanol which preferably is the main carbon source, is terminated or reduced for a time period sufficient to lower the concentration of the carbon source material substantially to a level at which the microorganisms substantially cease propagation. Preferably, this concentration is below about 0.005 and preferably between about 0.001-0.005 percent by volume of the liquid ferment medium. While this interruption of the carbon source feed can continue for any suitable length of time, it generally will last from about 1 to about 30 minutes and preferably from about 5 to about 15 minutes. The time period of interruption is sufficiently long so that upon restarting the microorganism will produce a toxic level of a biocidal agent such as an aldehyde. This time figure can vary depending upon the type of microorganism being cultured and the initial concentration of the carbon source in the fermentation medium. Preferably, during the interruption of the carbon source flow, the aeration and other fermentation conditions continue as before the interruption. Following the period of the interruption, the addition of the carbon source is resumed at a rapid rate and when the carbon source concentration by volume based on the liquid content, for methanol, is from about 0.1 to 1 and preferably from 0.1 to 0.25 percent there is generated by further fermentation, a sufficient quantity of formaldehyde to reach a toxic level and cause the death of substantially all the microbial cells. This biocidal concentration of formaldehyde will generally be above about 0.025 percent, and preferably between about 0.025 and 0.1 percent, by volume of the liquid ferment medium.

It is believed that the generated formaldehyde has a portion thereof contained within the cell and the remainder permeates from the cell into the fermentation medium. It is further believed that the analyzed formaldehyde level is that for the medium alone and does not include that contained within the cell. In any event, it has been found that when the above level is reached, an analyzed in the medium, there is a toxic amount of formaldehyde present.

The time needed to achieve the death of the microorganisms following the attainment of the carbon source concentration as described above is not particularly critical and death of the microorganisms appears to be very rapid once the levels of carbon source concentration disclosed above are reached after the interruption of the carbon source feed. The above description is directed toward a continuous fermentation process wherein the carbon source is fed at a substantially constant rate to the fermentation zone after a steady state operating condition of normal fermentation is achieved. In such continuous processes it is preferable that the carbon source feed be introduced into the fermentation zone admixed with the aqueous nutrient medium portion of the ferment medium required by the microbial cells for growth or propagation. However, is should be pointed out that this embodiment of the invention can also be practiced with batch type processes wherein the carbon source is introduced into the fermenter in small increments to maintain a desired carbon source concentration. It is desirable during the batch fermentation process that the carbon source addition be performed in small increments during fermentation because relatively high levels of the carbon source can be inhibitory or even toxic to the growth or propagation of the microbial cells.

In a second embodiment self toxification of the microbial cells can be accomplished by the generation of toxic levels of formaldehyde by decreasing the amount of dissolved oxygen in the fermentation medium. This can be accomplished in a plurality of ways as, for example, by reducing agitation, decreasing fermenter pressure and by a preferred method of interrupting or decreasing the input of oxygen to the fermentation medium. The fermentation medium is starved for oxygen for a period of time sufficient to lower the concentration of the dissolved oxygen substantially to a level at which the microorgamism substantially cease to propagate but yet not be rendered nonviable. This concentration of dissolved oxygen will be below about 10 and preferably below about 5 percent based on the saturation value under the same operating conditions. By starving the fermentation medium and hence the microbial cells of oxygen and thereby reducing the dissolved oxygen level, the propagation rate of the microbial cells is reduced to or near zero after a time period of starvation, the carbon source is allowed to build up and reach a level below a biocidal level, preferably between about 0.1 to 1 percent by volume based on the liquid content of the fermenter and more preferably between 0.1 and 0.25 percent as described above. As described above, the time to reach this level is not critical and may vary with the particular microorganism and fermentation process being conducted. However, it is well known in the art how to determine the carbon source concentration in the fermentation medium and whether or not the desired level of carbon source has been achieved. Once the carbon source level has been achieved the dissolved oxygen is rapidly increased and the microbial cells once again begin propagation and produce the abovedescribed toxic level of formaldehyde resulting in rendering the microorganisms non-viable. This second embodiment of the present invention is particularly well suited for continuous fermentation processes in which the carbon source and aqueous nutrient medium and oxygen are fed to the fermentation zone in a continuous manner. However, this embodiment is also adapted for practice in a batch type fermentation process as described above.

The above described embodiments of the present invention are simple to conduct and require no new equipment to practice. Irrespective of which of the embodiments is utilized, it is believed that the basis upon which self toxification of the microorganisms occurs is that the carbon source utilizing microorganism is capable of rapidy converting the carbon source to a biocidal agent or toxic metabolite such as an aldehyde, e.g., formaldehyde, but that the rate limiting step in the process is a conversion of the biocidal agent to other metabolic intermediates. Therefore when the first embodiment of the present invention is employed the microbial cells are first carbon source starved for a period of time and then exposed to relatively high concentration of the carbon source which the microorganisms rapidly convert to the biocidal agent. Because the microorganisms metabolize the biocidal agent slower than it is produced they are not able to dispose of the biocidal agent quickly enough whereby a toxic level is reached rendering the microorganism non-viable. In the second embodiment the interruption of the oxygen source effectively slows metabolism by the microorganisms of the carbon source and any other metabolic intermediates. After oxygenation is restarted, the carbon source concentration has been increased during the interruption to a relatively high level and the carbon source is rapidly converted to a biocidal agent which accomplishes the same result as the first embodiment. The above discussion of the mechanisms of the invention is a hypothesis.

It is known that aldehydes such as formaldehyde are biocidal agents and are effective for killing various types of microorganisms. However, the aldehyde in the present invention is produced by the microbial cells and it is believed that the biocidal properties of the aldehyde are more efficiently utilized by the microbial cells than the prior art method of adding formaldehyde from an external source to a microbial system. In the present invention the aldehyde is generated as a metabolic intermediate within the cell organism in sufficient quantities to quickly and effectively render the cells non-viable.

The generation of toxic levels of formaldehyde, which are capable of rendering the microorganism non-viable, utilizes such minute amounts of the toxic metabolite that additional treatment with heat or other added chemicals need not be employed to render the cells non-viable. Also, the amount of formaldehyde generated, including that released from the cell and retained in the cell, is believed to be so small that additional treatment steps beyond the usual washing and drying will not be needed to render the microbial product suitable for use in food applications and the like. The concentration of formaldehyde in the cells will be about 0.01 percent or less by weight and preferably between about 0.001 to 0.01 percent by weight of the cells.

The following example is provided to illustrate operability of the present invention.

EXAMPLE

A continuous aerobic fermentation run utilizing methanol as the carbon/energy source and covering a period of over 900 hours was terminated by causing the propagating microorganism *Hansenula polymorpha*, NRRL Y-11, 170 to generate toxic levels of formaldehyde in the fermenter thereby killing the microbial culture.

The fermentation run was started by charging a 4 liter fermentation vessel with 500 ml of an aqueous inoculum of *Hansenula polymorpha*, NRRL Y-11, 170 containing 1% by liquid volume of methanol along with Biotin ($6.4 \times 10^{-4}$ g/l) and Thiamine (0.064 g/l). The vessel also contained 2 liters of an aqueous mineral medium to sustain microbial growth. The aqueous mineral medium (2X FM-19 modified) was of the following composition:

| Component | Amount |
| --- | --- |
| $H_3PO_4$ (85%) | 5 ml |
| $CaSO_4 \cdot 2H_2O$ | 0.46 g |
| KOH | 1 g |
| $K_2SO_4$ | 3.5 g |
| $MgSO_4 \cdot 7H_2O$ | 3.0 g |
| Biotin | 0.00064 g |
| Thiamine | 0.064 g |
| Yeast Trace Mineral Solution[a] (10X No. 3) | 2 ml |
| Distilled Water | Make up to 1 liter |

(a) Composition of Yeast Trace Mineral Solution (10X No. 3) was as follows:

| Component | Amount |
| --- | --- |
| $CuSO_4 \cdot 5H_2O$ | 6 g |
| $ZnSO_4 \cdot 7H_2O$ | 18 g |
| $FeSO_4 \cdot 7H_2O$ | 65 g |
| $MnSO_4 \cdot 7H_2O$ | 4 g |
| Distilled Water | 1000 ml |

The fermentation vessel was equipped with stirring means (with RPM measurement), aeration means (both air and $O_2$ inlets), temperature measurement and control means, pH and dissolved oxygen measurement means, means for introducing continuously or intermittently several liquid streams and means for sampling the fermentation mixture to determine the concentration of microbial cells, methanol content and the like.

Ammonium hydroxide was fed to the fermentor as a separate liquid stream. The $NH_4OH$ served as a source of assimilable nitrogen for the culture. Methanol was fed to the fermentor as a separate liquid stream an contained 8 drops/l of a silicone type antifoaming agent (MAZU 37C, made by Mazer Chemical Co.). From hour 167 to about hour 497 in the run, the methanol stream also contained 1.2 ml/l of Yeast Extract solution (5 wt. % in $H_2O$). The Yeast Extract is obtainable from Difco Laboratories. The aqueous mineral medium described above was also fed to the fermentor as a separate liquid stream.

During the course of the run, the temperature was maintained at 40 to 46° C. and the pH was within the range of 3.3–3.7. The stirrer RPM was initially at 800 and was increased to 1000 after about 170 hours. Introduction of air to the fermentor was at rate of from 1.5 to 1.0 liters per minute (lpm) and an oxygen stream was fed at a rate of from 0.4 to 1.0 lpm. Introduction of the oxygen stream was begun after about 170 hours into the run. Both air and oxygen streams were shut off as described below in accordance with the instant invention in order to kill the growing culture.

At about 820 hours into the run the aqueous mineral feed medium was changed to one of the following composition (3X FM-20):

| Component | Amount |
| --- | --- |
| $H_3PO_4$ (85%) | 22.5 ml |
| $CaSO_4 \cdot 2H_2O$ | 1.035 g |
| $K_2SO_4$ | 15.75 g |
| $MgSO_4 \cdot 7H_2O$ | 13.5 g |
| KOH | 4.5 g |
| Biotin | 0.00064 g |
| Thiamine | 0.064 g |
| Yeast Trace Mineral Solution[a] (10X No. 4) | 9 ml |
| Distilled Water | Make up to 1 liter |

(a) Composition of Yeast Trace Mineral Solution (10X No. 4) was as follows:

| Component | Amount |
| --- | --- |
| $FeSO_4 \cdot 7H_2O$ | 65 g |
| $CuSO_4 \cdot 5H_2O$ | 6 g |
| $ZnSO_4 \cdot 7H_2O$ | 20 g |
| $MnSO_4 \cdot H_2O$ | 3 g |
| $H_2SO_4$ (conc.) | 5 ml |
| Distilled Water | 1000 ml |

At about 840 hours into the run the methanol feed again contained the Yeast Extract (2 ml/l of a 5% by wt. solution in $H_2O$).

During the course of the run, the retention time varied from 6.4 to 10.3 hours, and the yield of microbial cells ranged from about 26 to 32% by weight based on the methanol charged.

At 904 hours into the run, the air and oxygen streams were shut off for 40 minutes to initiate the self-toxification process of the instant invention. All other feed streams to the fermentor were kept flowing during this period. It was observed that the methanol content of the liquid phase increased from 0 to 0.2% (vol/vol) while the dissolved oxygen content dropped from 70 to 0% of the saturation value during the 40 minute oxygen starvation period. No peak due to formaldehyde was observed in gas-liquid phase chromatography (GLC) analysis of the fermentor liquid contents during the 40 minute oxygen starvation period. At the end of the 40 minute period, the air and oxygen streams were turned on again. Methanol content reached a peak level of 0.62% (vol/vol) after 10 minutes of restarting oxygen and air flow then slowly decreased, probably due to a stripping action by flowing gases. A distinct formaldehyde peak was observed in the GLC analysis within 10 minutes of restarting the oxygen and air flow. The presence of formaldehyde was also confirmed by a chemical colorimetric test on the fermentor liquid contents. The size of the GLC formaldehyde peak remained essentially constant over 15 minutes (3 samplings) and then slowly decreased probably due to a stripping action of the flowing gases. Thirty minutes after restarting the oxygen and air flow, the feed streams (methanol), aqueous minerals, the oxygen and air flow, the feed streams (methanol, aqueous minerals, $NH_4OH$) were shut off and the culture was observed to be dead.

The above run demonstrates the operability of the instant invention in causing the self-toxification of a yeast growing on methanol by oxygen starvation followed by reintroduction of oxygen whereby toxic levels of the metabolite formaldehyde were generated, thus killing the culture.

Reasonable variations and modifications, which will be apparent to those skilled in the art, can be made in this invention without departing from the spirit and scope thereof.

What is claimed and desired to be secured by Letters Patent is:

1. A self-toxification method for an aerobic fermentatation process utilizing oxygen and a carbon source in a fermentation medium in amounts sufficient for propagating at least one microorganism capable of generating a biocidal agent, said method comprising:
   (a) starving the microorganism of a growth essential material by lowering the concentration of growth essential material in the fermentation medium to a level at which the microorganism substantially ceases to propagate for a period of time sufficient to substantially cease the propagation of the microorganism;
   (b) after the propagation of the microorganism has substantially ceased, introducing the growth essential material into the fermentation medium in a quantity sufficient to cause the microorganism to generate a toxic concentration of a biocidal agent and thereby kill the microorganism, said quantity of growth essential material being less than the quantity of growth essential material necessary to kill the microorganism in the absence of the starvation step.

2. A method as set forth in claim 1 wherein said biocidal agent includes an aldehyde.

3. A method as set forth in claim 2 wherein said biocidal agent includes formaldehyde.

4. A method as set forth in claim 2 wherein said fermentation medium is liquid and said growth essential material is at least one growth essential material selected from a group consisting of a carbon source and an oxygen source.

5. A method as set forth in claim 4 wherein said growth essential material is the carbon source.

6. A method as set forth in claim 5 wherein said carbon source includes methanol as the main carbon source.

7. A method as set forth in claim 4 wherein said growth essential material is the oxygen source.

8. A method as set forth in claim 5 wherein said time period is substantially the time required for the carbon source concentration to fall below about 0.005 percent by volume of the fermentation medium.

9. A method as set forth in claim 4 wherein said toxic concentration of biocidal agent is above about 0.025 percent by volume of the fermentation medium.

10. A method as set forth in claim 7 wherein said oxygen source is the dissolved oxygen which is reduced to below about 10 percent of the saturation value under fermentation process conditions.

11. A method as set forth in claim 4 wherein said fermentation process is a batch process.

12. A method as set forth in claim 4 wherein said fermentation process is a continuous fermentation process conducted in a fermentation zone.

13. A method as set forth in claim 12 wherein a portion of the fermentation medium is withdrawn from the fermentation zone with steps (a) and (b) being performed on the thus removed portion of fermentation medium.

14. A method as set forth in claim 4 wherein said fermentation process is a foam process.

15. A method as set forth in claim 4 wherein: said biocidal agent comprises an aldehyde have from 1 to about 6 carbon atoms per molecule and said carbon source is selected from a group comprising alkanes and primary alcohols or mixtures of any two or more thereof.

16. An aerobic fermentation process for at least one microorganism capable of generating a biocidal agent comprising the steps of:
   (a) propagating said microorganism in a fermentation medium by introducing oxygen and a carbon source into the medium;
   (b) discontinuing the introduction of the oxygen or the carbon source or both sources into the medium for a period of time sufficient to lower the concentration of the discontinued source or sources said microorganism to substantially cease to propagate;

(c) reintroducing, after step (b), the discontinued source or sources in a quantity and for a time sufficient to cause the microorganism to generate a toxic concentration of a biocidal agent thereby killing the microorganism, said quantity being less than the quantity necessary to kill the microorganism in the absence of step (b); and (d) recovering the thus killed microorganism.

17. A process as set forth in claim 16 wherein a portion of the medium is removed from a fermenter in which the propagation is accomplished with steps (b), (c) and (d) being performed on the thus removed portion of medium.

18. A process as set forth in claim 16 wherein steps (b) and (c) are accomplished in a fermenter in which the propagation is accomplished.

19. A process as set forth in claim 16 wherein said carbon source is selected from a group comprising alkanes and primary alcohols or mixtures of any two or more thereof.

* * * * *

UNITED STATES PATENT AND TRADEMARK OFFICE
CERTIFICATE OF CORRECTION

PATENT NO. : 4,169,762

DATED : October 2, 1979

INVENTOR(S) : Donald O. Hitzman

It is certified that error appears in the above-identified patent and that said Letters Patent are hereby corrected as shown below:

Column 12, line 67 (claim 16), after "sources" insert --- in the medium causing ---;

Signed and Sealed this

Tenth Day of August 1982

[SEAL]

Attest:

Attesting Officer

GERALD J. MOSSINGHOFF

Commissioner of Patents and Trademarks